(12) United States Patent
Sherwinter

(10) Patent No.: US 9,861,356 B2
(45) Date of Patent: Jan. 9, 2018

(54) SUTURING DEVICE AND METHOD

(71) Applicant: Danny Sherwinter, Brooklyn, NY (US)

(72) Inventor: Danny Sherwinter, Brooklyn, NY (US)

(73) Assignee: Brainchild Surgical Devices LLC, Brooklyn, NY (US)

( * ) Notice: Subject to any disclaimer, the term of this patent is extended or adjusted under 35 U.S.C. 154(b) by 529 days.

(21) Appl. No.: 14/503,648

(22) Filed: Oct. 1, 2014

(65) Prior Publication Data

US 2016/0095589 A1 Apr. 7, 2016

(51) Int. Cl.
*A61B 17/04* (2006.01)
*A61B 17/00* (2006.01)
*A61B 17/06* (2006.01)

(52) U.S. Cl.
CPC .. *A61B 17/0482* (2013.01); *A61B 2017/0042* (2013.01); *A61B 2017/06042* (2013.01)

(58) Field of Classification Search
CPC ........ A61B 17/0482; A61B 2017/0042; A61B 2017/06042; A61B 17/04; A61B 17/34; A61B 17/0485; A61B 17/0483; A61B 17/0469; A61B 17/3403; A61B 17/3423; A61B 2017/00663; A61B 2017/0474
USPC ........................................................ 606/148
See application file for complete search history.

(56) References Cited

U.S. PATENT DOCUMENTS

| 5,330,488 A | 7/1994 | Goldrath |
| 5,336,239 A | 8/1994 | Gimpelson |
| 5,439,469 A | 8/1995 | Heaven et al. |
| 5,470,338 A | 11/1995 | Whitfield et al. |
| 5,499,991 A | 3/1996 | Garman et al. |
| 5,722,981 A | 3/1998 | Stevens |
| 5,817,110 A | 10/1998 | Kronner |
| 5,817,112 A | 10/1998 | Christoudias |
| 6,183,485 B1 | 2/2001 | Thomason et al. |
| 6,428,549 B1 * | 8/2002 | Kontos .............. A61B 17/0057 606/139 |
| 6,743,241 B2 | 6/2004 | Kerr |
| 7,449,024 B2 | 11/2008 | Stafford |
| 8,376,932 B2 | 2/2013 | Hashiba et al. |

(Continued)

FOREIGN PATENT DOCUMENTS

EP 0542428 A1 * 5/1993 ......... A61B 17/3417

OTHER PUBLICATIONS

Carter-Thomason Closesure System brochure. Published 2011 Cooper Surgical, Inc. 81821 Rev. Jul. 2011.

*Primary Examiner* — Christopher L Templeton
*Assistant Examiner* — George J Ulsh
(74) *Attorney, Agent, or Firm* — Marsh Fischmann & Breyfogle LLP; Daniel J. Sherwinter

(57) ABSTRACT

A suturing device and method of use involve inserting the device into a hole, positioning material around the hole into a notch of the device, passing a needle through a cavity in the device and the material positioned in the notch, and lining up an eye of the needle with a portal for passage of a suture. A suture is then passed through the eye of the needle and the needle is removed from the material (such as skin and fascia) with the suture. The suture is then removed and the process is repeated with another end of the suture at another location through the material, around the hole. When the suture is passed through the second point of penetration, the suture now extends both into and out of the material at different points around the hole and can be tied.

9 Claims, 19 Drawing Sheets

(56) References Cited

U.S. PATENT DOCUMENTS

| | | |
|---|---|---|
| 8,591,529 B2 | 11/2013 | Smith |
| 2005/0192597 A1 | 9/2005 | Boebel et al. |
| 2007/0129735 A1* | 6/2007 | Filipi ................ A61B 17/0469 |
| | | 606/144 |
| 2007/0213757 A1 | 9/2007 | Boraiah |
| 2010/0324573 A1 | 12/2010 | Toubia et al. |
| 2013/0012964 A1 | 1/2013 | Warnock |
| 2013/0035700 A1 | 2/2013 | Heneveld |
| 2013/0165955 A1 | 6/2013 | Chin |
| 2013/0165956 A1* | 6/2013 | Sherts ................ A61B 17/0482 |
| | | 606/148 |
| 2013/0345724 A1 | 12/2013 | van der Burg et al. |
| 2014/0107672 A1 | 4/2014 | Dross |

* cited by examiner

SUTURING DEVICE AND METHOD

FIELD OF THE DISCLOSED TECHNOLOGY

The disclosed technology relates generally to surgical and mending devices and, more specifically, towards a device for suturing or closing an opening.

BACKGROUND OF THE DISCLOSED TECHNOLOGY

In standard surgical practice and, specifically in minimally invasive surgical procedures, incisions are made in the skin, subcutaneous fat, fascia, and muscle tissue. Using standard surgical techniques, instruments are introduced through these defects to perform surgery. These defects must be closed, usually with sutures, at the conclusion of a procedure, to prevent herniation and other complications at these sites.

Prior art methods used to close tissue defects (or, alternatively, which may be used to close any hole where one has ready/direct access only to one side thereof) usually involve the use of curved needles. Some of the technologies require placing a suture through the skin, then grasping the suture extending freely in the air under camera guidance. This task can be extremely difficult even in experienced hands. An additional drawback of the existing techniques is the excessive cost of usually disposable, specialized guide devices for each procedure which is unacceptable to hospitals and surgery centers. While sometimes the aforementioned guides or other tools may be employed to aid in the use thereof, one must rely solely on feeling one's way through a cavity, and/or looking in a camera, while at the same time, risking injury to bowels, blood vessels, or other intra-abdominal organs. This may lead to sepsis, hemorrhage, and even death. The current methods are cumbersome and require a significant learning curve for a practitioner to become proficient in the techniques.

There exists a need for a method and device which is easy to use, has a shorter learning curve than current techniques, and which reduces risk of internal injury to the patient. Still further, a reduction in the cost of surgery and, of course, the expense of errors, is needed in the art.

SUMMARY OF THE DISCLOSED TECHNOLOGY

It is therefore an object of the disclosed technology to provide a safe, low cost suturing method and device which is easy to use for suturing tissue defects. It is a further object to suture any other hole or portal, including those where direct access is available only to one side thereof. "Direct access" is defined as being able to touch an entire side of a work surface, as opposed to "indirect access" which requires first passing through the work surface.

In one embodiment of the disclosed technology, a suturing kit includes an elliptical cone having a base and an apex at opposite ends, as well as a needle. The base of the elliptical cone can or does form a unitary structure with an elongated handle, such that an acute, obtuse, or right angle is formed between the elongated handle and a side of the elliptical cone that is adjacent to the handle. A notch is cut into one side of the elliptical cone, extending partially between the base and the apex.

The elliptical cone can or does include at least one needle guide cavity extending in a straight path from a needle guide portal at the base of the cone and through the base of the cone. The needle guide cavity is then interrupted by the notch, but otherwise continues through the cone towards the apex. An exit portal is situated between the notch and the apex of the cone, and extends substantially perpendicular to, and joins with, the needle guide cavity, the cavity terminating, in some embodiments, before the apex. The needle included in the kit has an eye therein. The needle further can or does have a length that is longer than the needle guide cavity, such that the eye can align with the exit portal when the needle is inserted in the needle guide portal, such as when the needle is fully inserted therein.

The elliptical cone of the suturing kits, in embodiments of the disclosed technology, additionally includes at least one curved suture guide cavity. The suture guide cavity extends between a suture guide portal located substantially or exactly at the base of the elliptical cone, and at a point that is between the notch and the exit portal of the elliptical cone.

In a further embodiment of the disclosed technology, a suturing device includes a base and an apex, the base and the apex being located at opposite ends of the suturing device. A notch is cut (defined as "a break in an otherwise continuous structure, whether removed from the structure after production thereof, or produced without the lacking part") into one side of the suturing device. The notch extends partially between the base and the apex. The suturing device further includes at least one needle guide cavity at the base, in this embodiment, extending in a straight path through the suturing device between the base and the notch, as well as between the notch and the apex. An exit portal is situated between the notch and the apex of the suturing device.

The device can or does have at least one curved suture guide cavity extending between a suture guide portal located substantially at the base and opening into the needle guide cavity, at a point between the notch and the exit portal of the suturing device.

In some embodiments, the suturing device can have a portion thereof in the shape of an elliptical cone, which, for purposes of this disclosure, can include a blunt apex at the tip of the device. The base of the elliptical cone can form a unitary structure with a handle, such that an acute, right, or obtuse angle is formed between the handle and a side of the elliptical cone adjacent to the handle. The needle guide cavity of the suturing device can terminate at a point before the apex. The suture guide portal may be located closer to the base than the apex of the suturing device, or, alternatively, the suture guide portal can be located at the base of the suturing device.

A method of suturing is also claimed. A first step includes inserting an apex of a suturing device into a pre-existing hole until material around the hole is positioned within a notch. The notch is cut into on one side of the suturing device between a base and the apex thereof, such that the base and the apex are located at opposite ends of the suturing device. A needle, with an eye, is inserted through a needle guide portal of the suturing device and is pushed through the material positioned within the notch (e.g., skin or other tissues) and continues until the eye of the needle aligns with an exit portal of the suturing device. The exit portal is, or can be, situated between the notch and the apex of the suturing device.

Still describing the current method, a first end of a first suture is then inserted through a suture guide portal of the suturing device and pushed through the eye of the needle, as well as through the exit portal. The needle is then at least partially extracted from the suturing device until the suture, still passing through the eye of the needle, passes back through the material at a point of the penetration, pulling the suture there-through. The suturing device is rotated with respect to the hole, such that insertion of the needle now can proceed at a second point of penetration of the material. Then, the process of inserting the needle and passing the suture (at a second end thereof) is repeated a second time, or as many times as needed to close the hole. The suture device can then be extracted from the hole. When the suture is passed through the second point of penetration, the suture now extends both into and out of the material at different points around the hole and can be tied.

The pre-existing hole can be a tissue defect, and the material around the hole can constitute bodily tissue. The method can first include a step of removing a trocar from a tissue defect before the first step of inserting the suturing device. The step of inserting an apex of a suturing device into a pre-existing hole can further include rotating and manipulating the device while maximizing an amount of tissue positioned in the notch. The suture guide portal can be located substantially at the base of the suturing device. Alternatively, the suture guide portal can be located at the base of the suturing device.

The step of at least partially extracting the needle can further include completely extracting the needle from the suturing device. The step of rotating the suturing device can further include rotating the device substantially 180 degrees. The suturing device can be elliptical, such that rotating the device substantially 180 degrees causes the tissue defect to stretch, such that first and second points of penetrating are spaced further apart than carrying out the method with a corresponding circular device. The step of extracting the suture device can further include a step of securing the ends of the suture and suturing the pre-existing hole. The first suture can be looped through a second suture, such that each end of the first and second sutures can be inserted through the suture guide portal after each step of inserting the needle and penetrating the material.

In an alternative embodiment of the technology disclosed, a method of suturing includes a first step of inserting a suturing device into a pre-existing hole, until material around the hole is positioned within a notch cut into one side of the suturing device. The notch is situated between a base and an apex, wherein the base and the apex are located at opposite ends of the suturing device. A needle having an eye is inserted though the suturing device. The inserted needle penetrates the material and is continually inserted until the eye of the needle aligns with an exit portal of the suturing device. The exit portal is situated between the notch and the apex of the suturing device. A first end of a suture is inserted through a suture guide portal of the suturing device, and is then pushed through the eye of the needle and through the exit portal. The needle is at least partially extracted from the suturing device until the suture, still passing through the eye of the needle, passes through the material at a point of the penetration. The steps of: penetrating the material at a second point on the material, inserting a second end of the suture through the suture guide portal, and at least partially extracting the needle until the suture passes through the material a second time, are carried out in this embodiment.

The suturing device can be substantially formed of an elliptical cone, with the exit portal at a tapered end thereof. The step of inserting a suturing device can further include inserting an apex of a suturing device into a pre-existing hole, and can further include a step of rotating and manipulating the device, so that a maximal amount of material is positioned in the notch.

The step of inserting a needle can include inserting a needle through a needle guide portal at the base of the suturing device, and the material penetrated can be the material positioned within the notch. The suture guide portal can be located substantially at the base of the suturing device. The step of at least partially extracting the needle can encompass completely extracting the needle from the suturing device, further include a step of rotating the suturing device with respect to the hole, and the step of rotating can encompass rotating the device substantially 180 degrees.

The suturing method can further include a subsequent step of extracting the suture device from the hole, and can further include a step of securing the ends of the suture, suturing the pre-existing hole, after the step of at least partially extracting the needle a second time is carried outs.

The term "substantially" is defined as "considered to be so by one having ordinary skill in the art of suturing," and/or "at the side described or an adjacent side," and/or "at least 90% of the term being modified by 'substantially.'"

The terms "or" and "and/or" should be interpreted as being inclusive of one or both terms being joined thereby. For example, in the set {A, B}, the phrase "A or B" includes "A," "B," and "A and B."

DETAILED DESCRIPTION OF EMBODIMENTS OF THE DISCLOSED TECHNOLOGY

Embodiments of the disclosed technology comprise a safe and low cost suturing device and method that is also simple to use. The suturing device and method can be used for suturing tissue defects, or, for suturing and closing any other hole or portal where one has direct access only to one side thereof. The structure of the suturing device allows the device to be manipulated easily and accurately. Embodiments of the suturing device include a closed housing for an inserted needle, which prevents the needle's sharp tip from being freely situated in the abdominal cavity.

Embodiments of the disclosed technology will become clearer when reviewed in connection with the description of the figures herein below.

Figure 1:
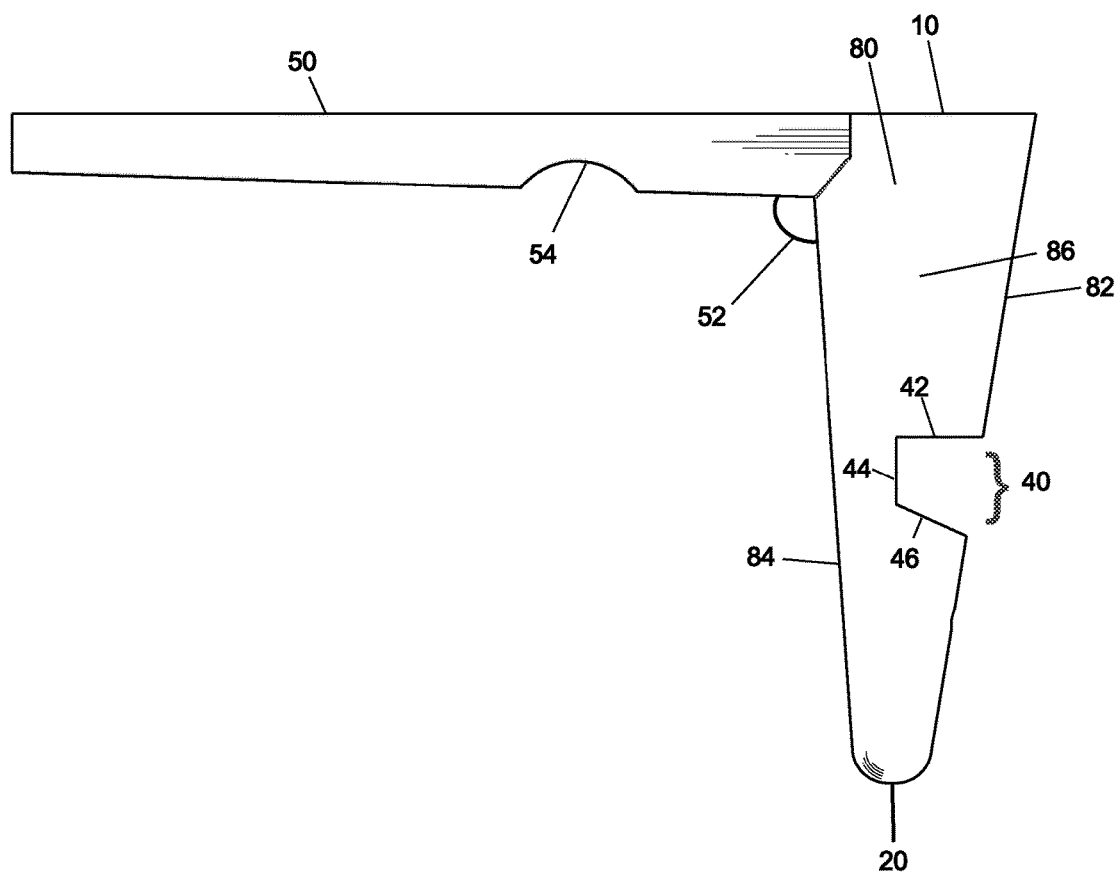
FIG. 1 shows a side elevation view of a suturing device in an embodiment of the disclosed technology.

FIG. 1 shows a side elevation view of a suturing device of embodiments of the disclosed technology. The suturing device of this embodiment is an elliptical cone 80 having a base 10 at a first end and an apex 20 at a second, opposite, end. FIG. 1 shows a side 86 of the elliptical cone. The term "elliptical cone" is defined herein as a geometric cone with a notch cut into a part thereof. The elliptical cone may be elongated in one dimension, such that the base is in the shape of an oval. In an alternative embodiment, any elongated member may be used.

A notch 40 is cut into a front side 82 (the front side 82 is opposite the side 84 adjacent to the handle) of the elliptical cone 80, the notch 40 also extending partially into adjacent and opposing sides 86, and partially between the base 10 and the apex 20 of the elliptical cone. The term "cut into" is defined as "preformed" or "removed from the described mathematically defined structure" and defines a part of a device which is lacking from the otherwise described structure. The construction thereof need not actually be "cut" from the structure after it is produced, but rather can be produced with the lack of the portion described as being "cut into" such a shape. While the notch 40 is cut into the front side 82 in this embodiment, the notch 40 can be cut into any side of the elliptical cone 80 and still be in the scope of the disclosed technology.

The notch has a top surface 42 which defines a region of the elliptical cone between the base 10 and notch 40. The notch has a bottom surface 46 which defines a region of the elliptical cone between the apex 20 and the notch 40. A back surface 44 of the notch forms the back side thereof can be substantially parallel, in embodiments of the disclosed technology, to the adjacent side 84 opposite the notch of the cone region. A continuous plane or surface is formed between the apex 20, base 10 (circumscribed also by back side 84), and back surface 44 of the notch. Still further, the bottom surface 46 may for an acute or obtuse angle relative to the back surface 44 and/or the adjacent side 84 which helps ease removal of the device from the hole being sewn.

Figure 2:
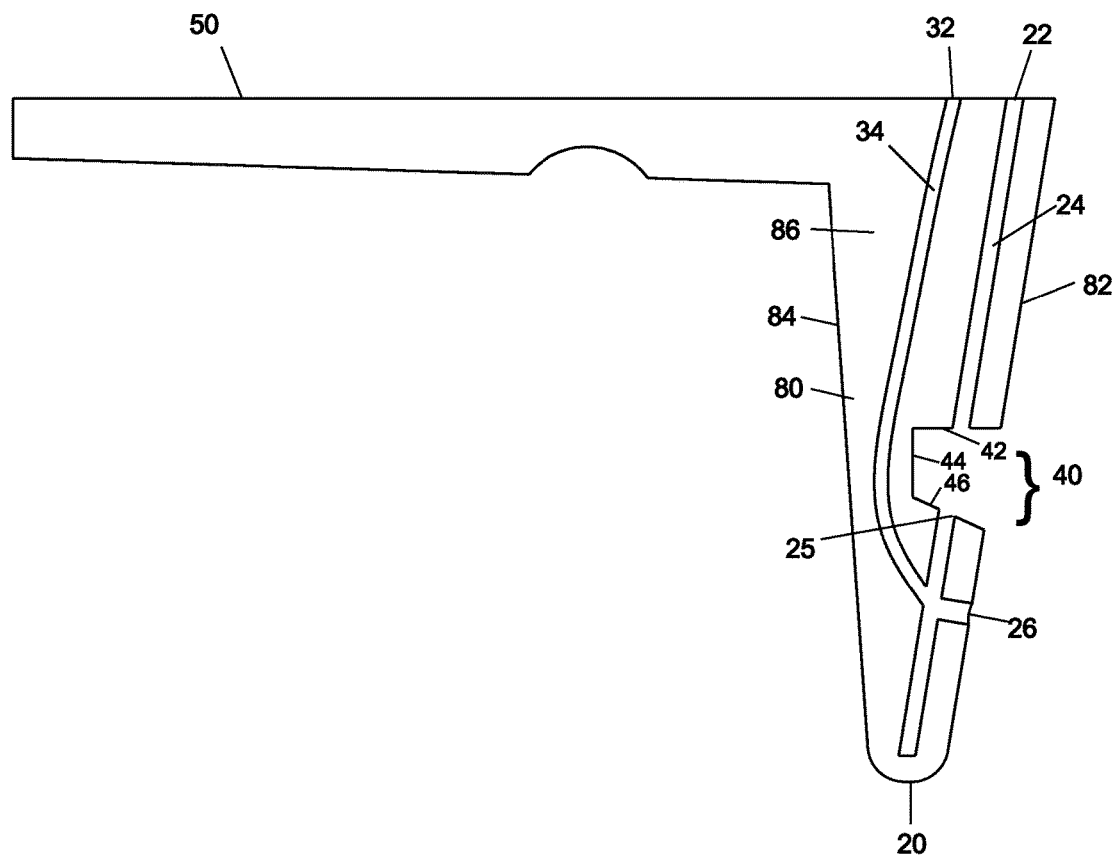
FIG. 2 shows a cutaway view of the side elevation view of the suturing device shown in FIG. 1.
Figure 8:
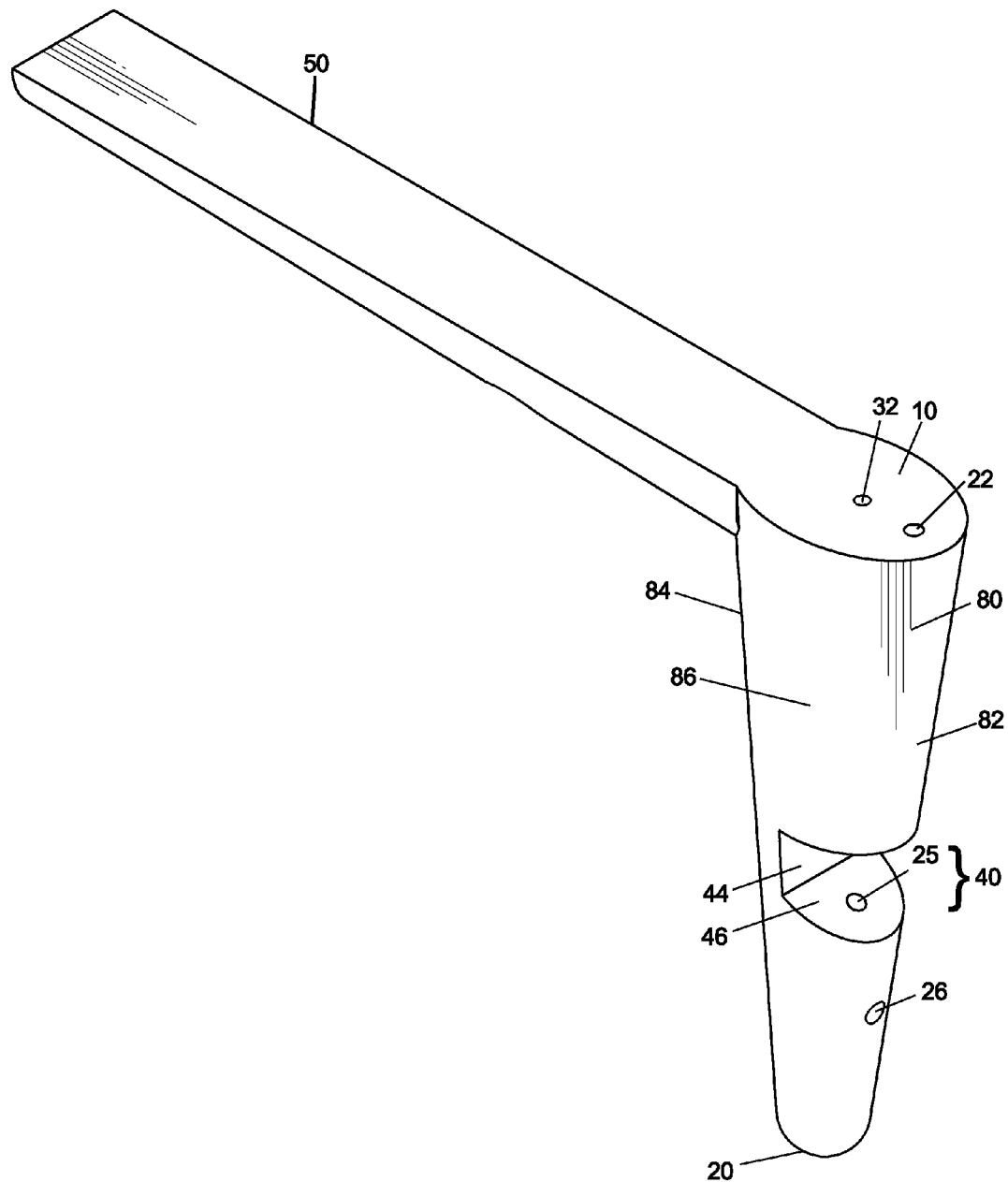
FIG. 8 shows a top and front side perspective view of a suturing device, in an embodiment of the disclosed technology.

FIG. 2 shows a cutaway view of the side elevation view of the suturing device shown in FIG. 1. FIG. 8 shows a top and front side perspective view of a suturing device in an embodiment of the disclosed technology. Now discussing FIGS. 2 and 8 simultaneously, a needle guide cavity 24 and a suture guide cavity 34 extend into the body of the elliptical cone 80. In embodiments, the needle guide cavity 24 extends in a straight path from a needle guide portal 22 at the base 10 of the elliptical cone 80, and through the body of the cone 80. The needle guide cavity 24 is then interrupted by the notch 40, after which it continues through a second needle guide portal 25 located on the bottom side 46 of the notch 40, and continues through the cone 80 towards the apex 20.

An exit portal 26 is situated on the front side 82 of the elliptical cone, between the notch 40 and the apex 20 of the cone 80. The exit portal 26 may be on side of the device, including at the apex thereof. The exit portal 26 extends substantially perpendicular from the needle guide cavity 24 at a point between the second needle guide portal 25 and a point of termination of the needle guide cavity. The needle guide cavity 24 terminates, in some embodiments, at a point before the apex 20.

The suture guide cavity 34 extends between a suture guide portal 32 located at the base 10 of the elliptical cone, and a point located between the notch 40 and the exit portal 26 of the elliptical cone 80. The suture guide portal 32 can be located substantially at the base 10, defined as located closer to the base 10 than the apex 20 of the suturing device, or, alternatively, the suture guide portal 32 may be located exactly at the base 10 of the suturing device. As shown in FIG. 2, the suture guide cavity 34 is curved and joins the needle guide cavity 24 at a point between the bottom side 46 of the notch 40 and the exit portal 26. The suture guide cavity 34 joins with, and forms a unitary cavity with, the exit portal 26 via the needle guide cavity 24.

Figure 3:
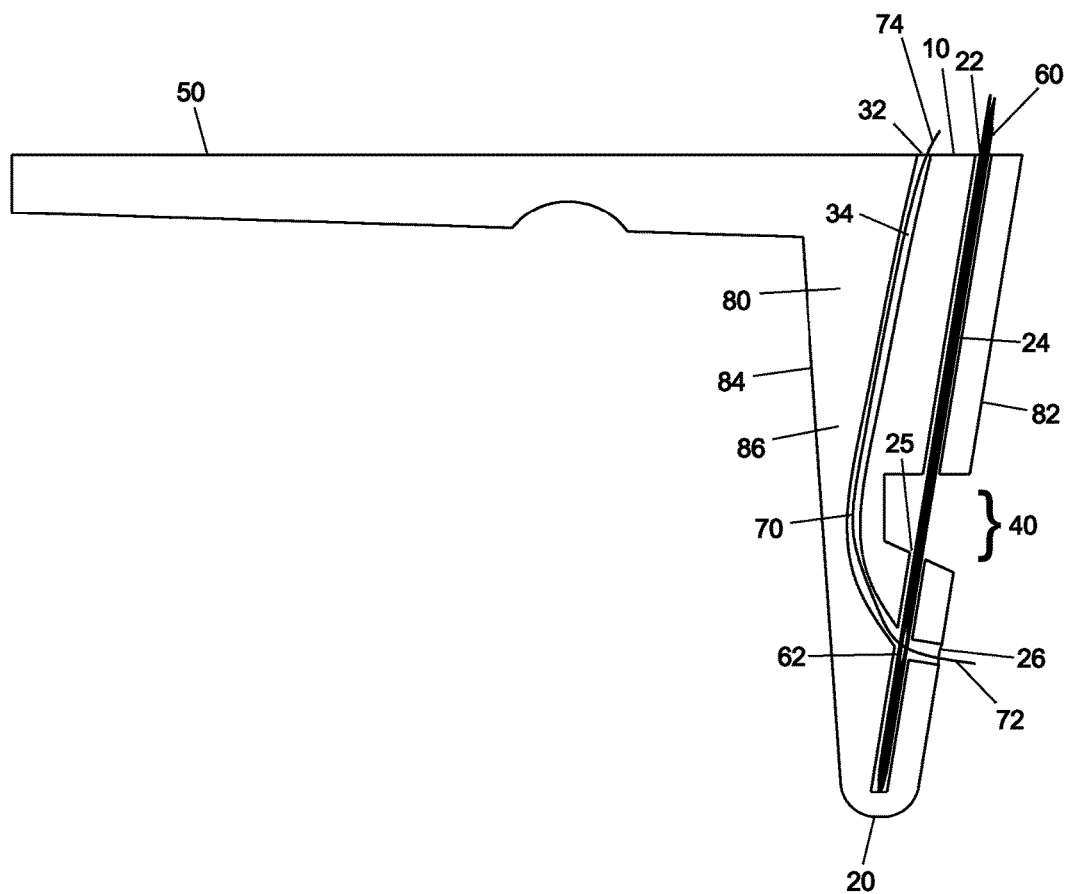
FIG. 3 shows a cutaway side elevation view of a suturing device with a needle and a suture inserted therein, in an embodiment of the disclosed technology.
Figure 9:
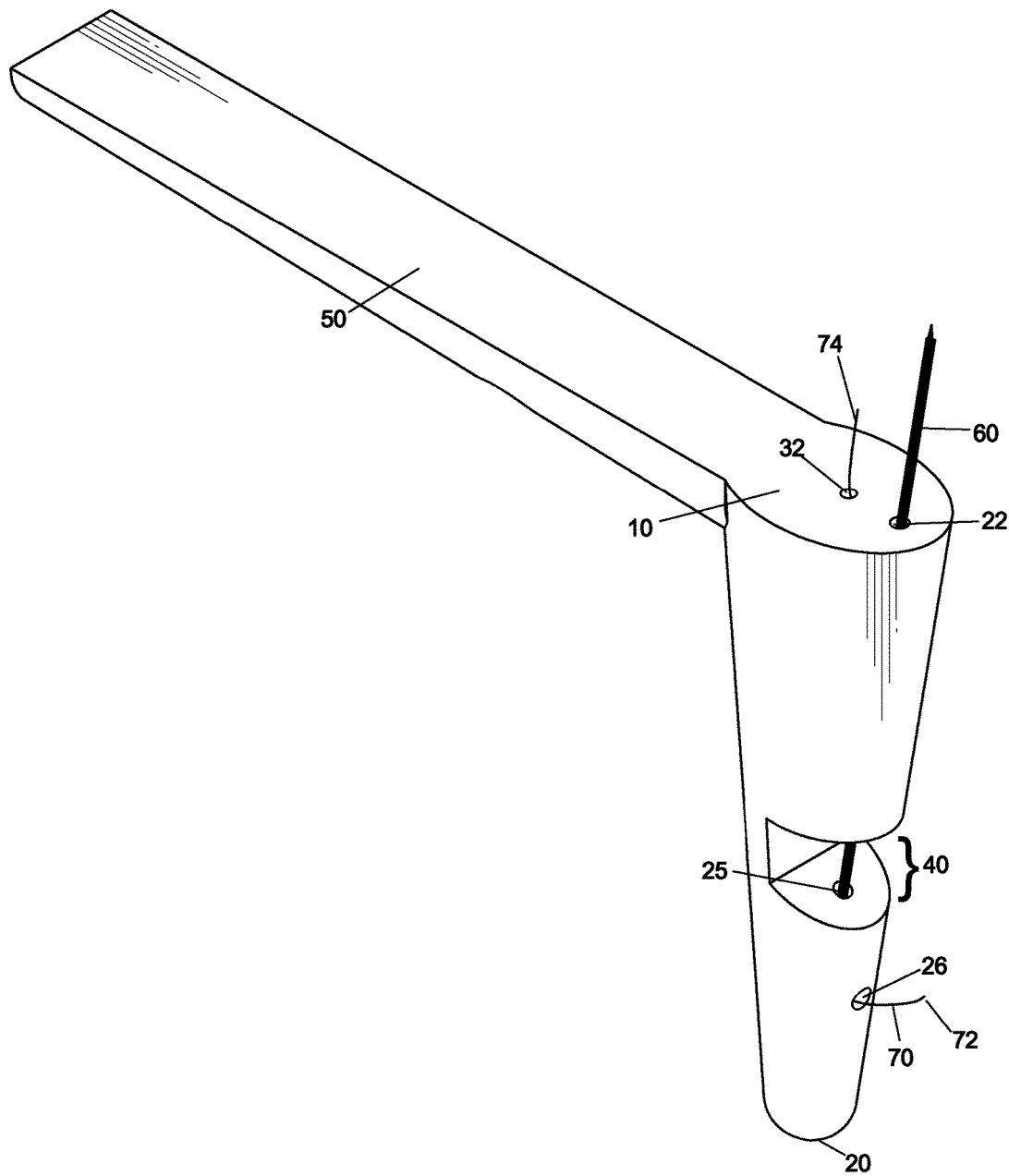
FIG. 9 shows a top and front side perspective view of a suturing device, having a needle and a suture inserted, in an embodiment of the disclosed technology.

FIG. 3 shows a cutaway side elevation view of a suturing device with a needle 60 and a suture 70 each inserted therein, in an embodiment of the disclosed technology. FIG. 9 shows a top and front side perspective view of a suturing device having a needle 60 and a suture 70 each inserted therein, in an embodiment of the disclosed technology. Now discussing FIGS. 3 and 9 simultaneously, in embodiments of the disclosed technology, the eye 62 of the needle 60 aligns with the exit portal 26 when the needle is inserted into the needle guide portal 22, past the notch 40, and at least reaching the exit portal 26. The needle 60 has an eye 62 and can or does have a length that is longer than the needle guide cavity 24. In embodiments of the disclosed technology, the eye 62 aligns with the exit portal 26 when the needle 60 is completely inserted in the needle guide cavity 24, such that the tip of the needle is in contact with the bottom of the needle guide cavity 24. The needle 60 can be seen in the notch 40 when the needle 60 is inserted into the needle guide portal 22 and at least passes through the notch 40. Still further, the needle guide cavity 24 and/or the needle guide portal 22 can have an oval or oblong shape, forcing the needle 60 to be oriented such that the eye 62 of the needle 60 faces the exit portal 26 when the needle is inserted in the cavity.

The term "suture" is defined herein as an elongated, flexible string, thread, sinew, strand, and so on. The suture 70 has a first end 72 and a second end 74, and has a length that is longer than the length of the area between the suture guide portal 32 and the exit portal 26. Upon insertion through the suture guide portal 32, and upon being pushed through the curved suture guide cavity 34, the first end 72 of the suture 70 passes through the eye 62 of the needle 60 aligned with the exit portal 26, and exits through the exit portal 26 at substantially 90 degrees. A "double suture" can also be used with embodiments of the disclosed technology, having two strands which connect at a central area forming an "X" configuration. The method of use is otherwise the same, repeated with each of the four ends of such a suture.

Figure 4:
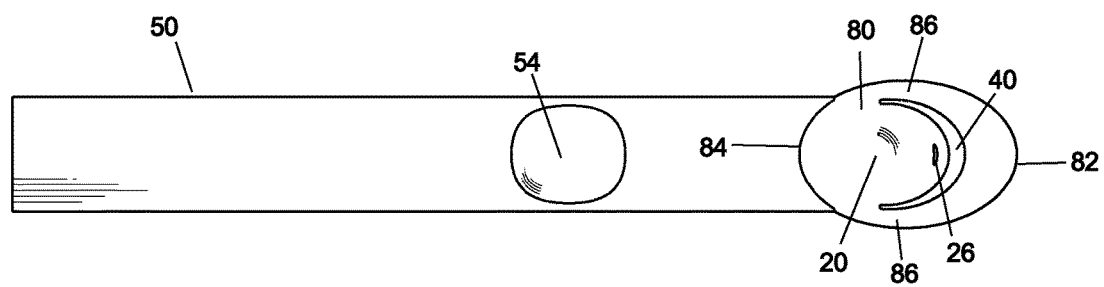
FIG. 4 shows a bottom plan view of a suturing device, in an embodiment of the disclosed technology.

FIG. 4 shows a bottom plan view of a suturing device in an embodiment of the disclosed technology. The bottom surface of the unitary handle 50 is shown with the indentation 54 for finger placement that aids in gripping the device. The elliptical cone 80 portion is shown extending from the base and narrowing until terminating at the narrowest point shown, the apex 20. The notch 40 is shown cut into the front side 82 of the cone 80 and in between the base 10 and the apex 20 of the cone 80.

Figure 5:
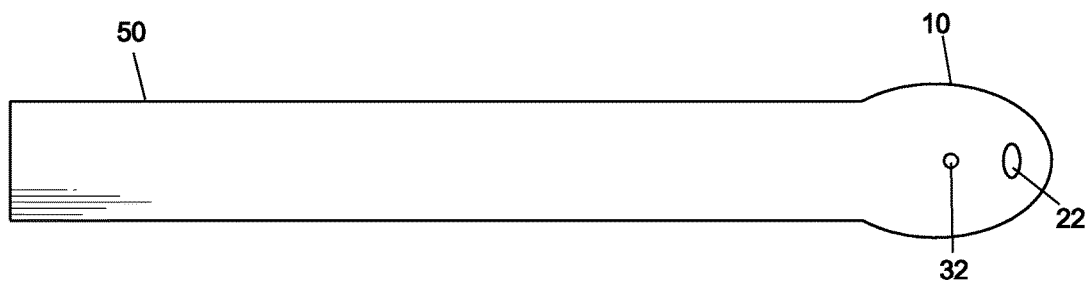
FIG. 5 shows a top plan view of a suturing device, in an embodiment of the disclosed technology.

FIG. 5 shows a top plan view of a suturing device, in an embodiment of the disclosed technology. In embodiments, the needle guide portal 22 and the suture guide portal 32 are situated linearly at the base 10 of the cone 80. The base is an ellipse in embodiments of the disclosed technology. The elongated handle can extend in the same line from the base 10 as the needle and suture guide portals 22 and 32 discussed above. In further embodiments, the handle need not be used. Rather, the elongated portion of the device 80 is used without a handle portion 50.

Figure 6:
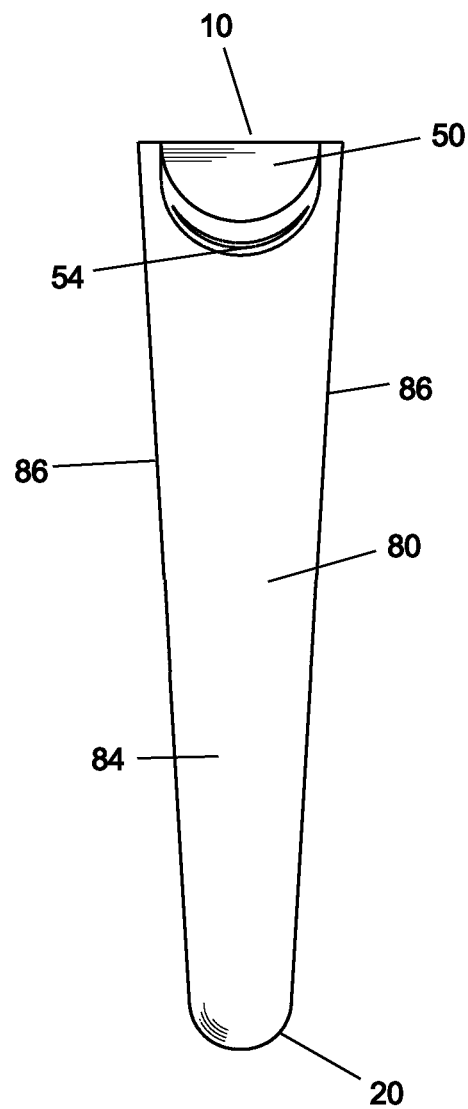
FIG. 6 shows a back side elevation view of a suturing device, in an embodiment of the disclosed technology.
Figure 10:
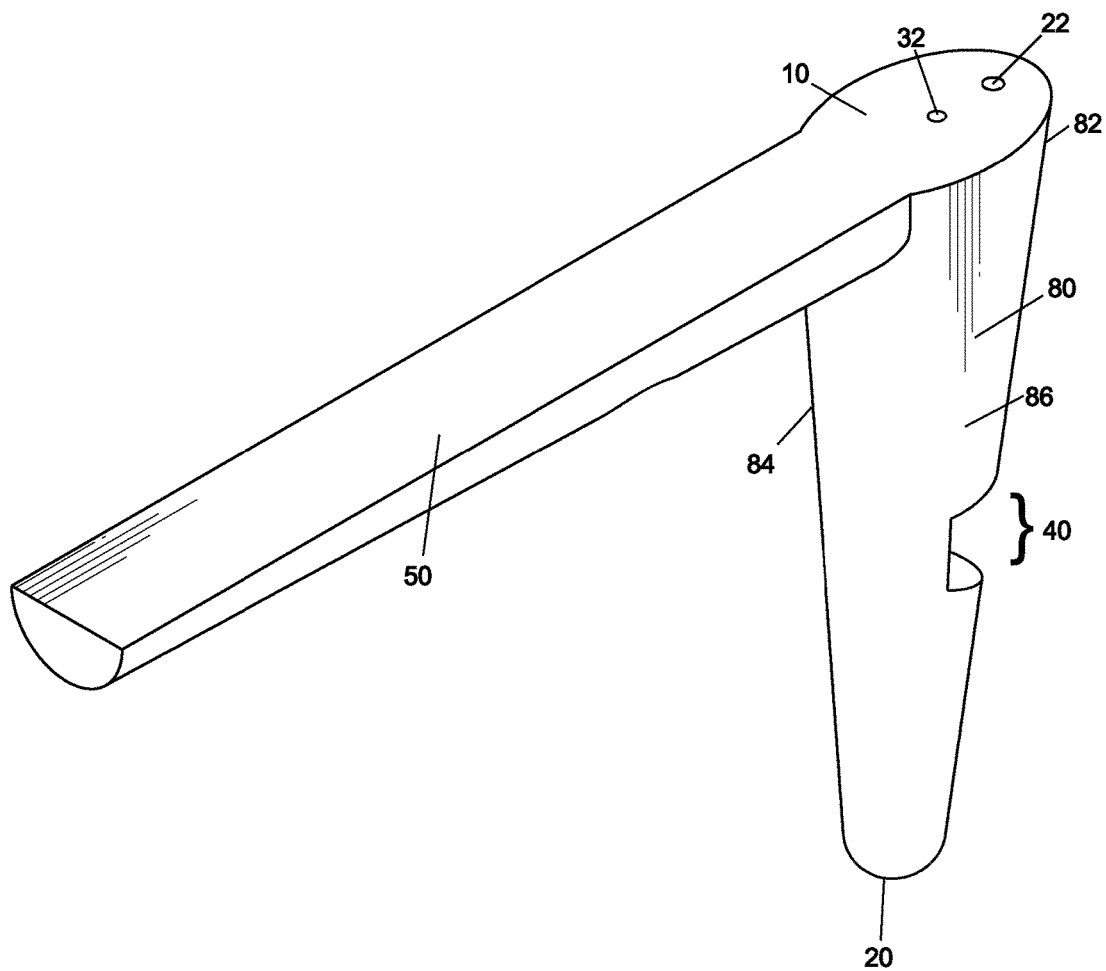
FIG. 10 shows a top and back side perspective view of a suturing device, in an embodiment of the disclosed technology.

FIG. 6 shows a back side elevation view of a suturing device in an embodiment of the disclosed technology. FIG. 10 shows a top and back side perspective view of a suturing device in an embodiment of the disclosed technology. Discussing FIGS. 6 and 10 simultaneously, the back side 84 of the elliptical cone 80 adjacent to the elongated handle 50 extends downward from the base 10, terminating at the apex 20. The handle is shown extending from the point where it meets the elliptical cone forming the acute or 90 degree angle 52, up to the tip of the handle 50. In embodiments, the finger indentation 54 is situated between the tip of the handle 50 and the angle 52 formed, where the handle 50 meets the elliptical cone 80. The notch 40 is partially cut into the side 86 of the elliptical cone between the front side 82 and the back side 84, adjacent to the elongated handle.

Figure 7:
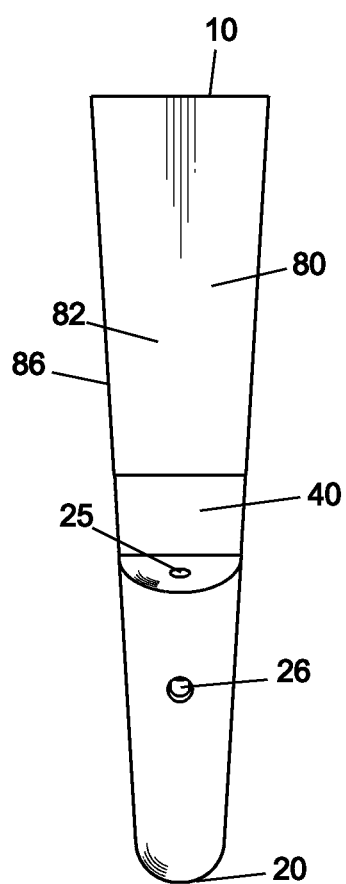
FIG. 7 shows a front side elevation view of a suturing device, in an embodiment of the disclosed technology.

FIG. 7 shows a front side elevation view of a suturing device of an embodiment of the disclosed technology. In this figure, the notch 40 can be seen cut into the front side 82 of the elliptical cone portion 80, in embodiments of the disclosed technology. The second needle guide portal 25 of the needle guide cavity 24 is located on the bottom surface 46 of the device, forming the notch 40. The exit portal 26, situated perpendicularly to the needle guide cavity 24, is located at a point below the notch 40, and before the termination of the needle guide cavity 24. In another embodiment of the disclosed technology, the suture guide and needle guide cavities may be at any angle to each other and to the exterior of the suturing device as long as the cavities cross each other at some point.

Figure 11:
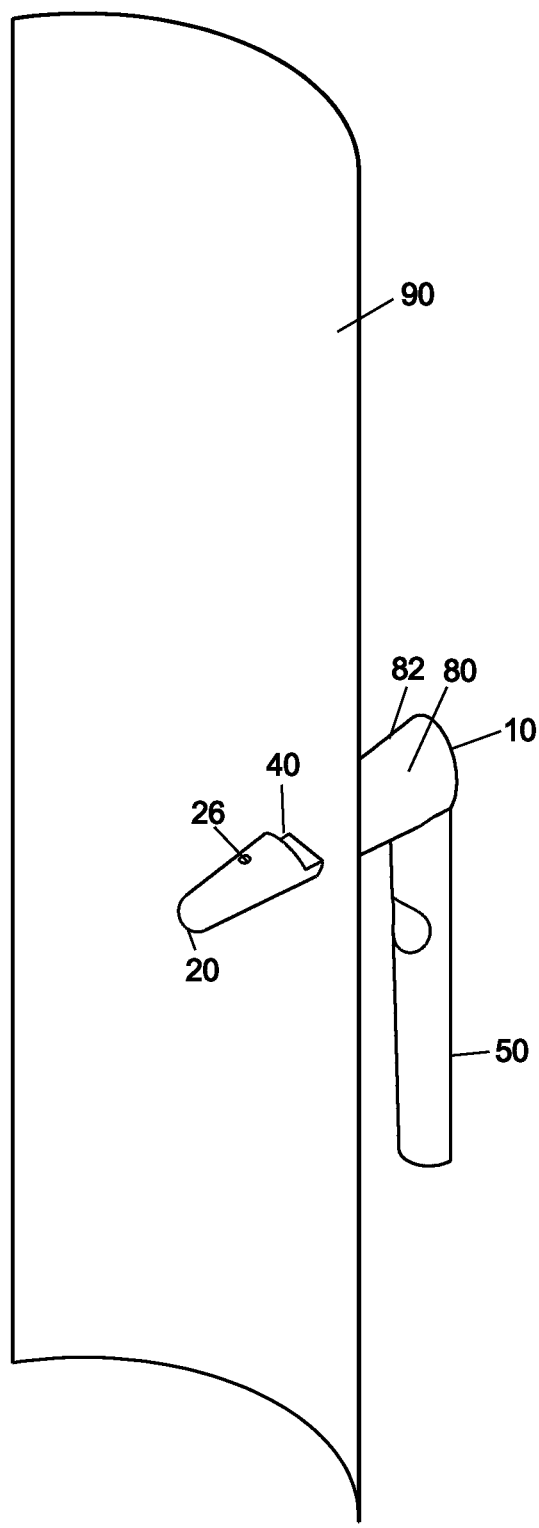
FIG. 11 shows a bottom and front side perspective view of a suturing device inserted into material, in an embodiment of the disclosed technology.
Figure 12:
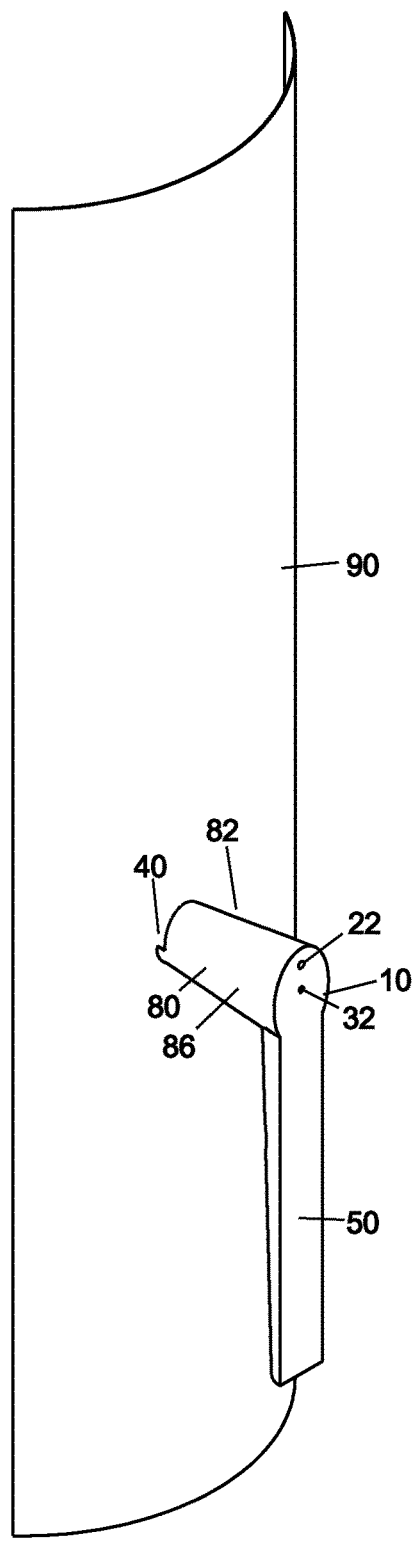
FIG. 12 shows a top and front side perspective view of a suturing device inserted into material, in an embodiment of the disclosed technology.

FIG. 11 shows a bottom and front side perspective view of a suturing device inserted into material, in an embodiment of the disclosed technology. FIG. 12 shows a top and front side perspective view of a suturing device inserted into material, in an embodiment of the disclosed technology. Now discussing FIGS. 11 and 12 simultaneously, the apex 20 of the suturing device is inserted into a preexisting hole in material 90. The device is inserted into the hole until the material 90 surrounding the hole is positioned in the notch 40. The base 10, elongated handle 50, and top portion of the elliptical cone 80 (extending between the base 10 and the notch 40) remain visible above the material. The bottom portion of the cone 80 extending between the notch 40 and the apex 20 are visible from beneath the material.

Figure 13:
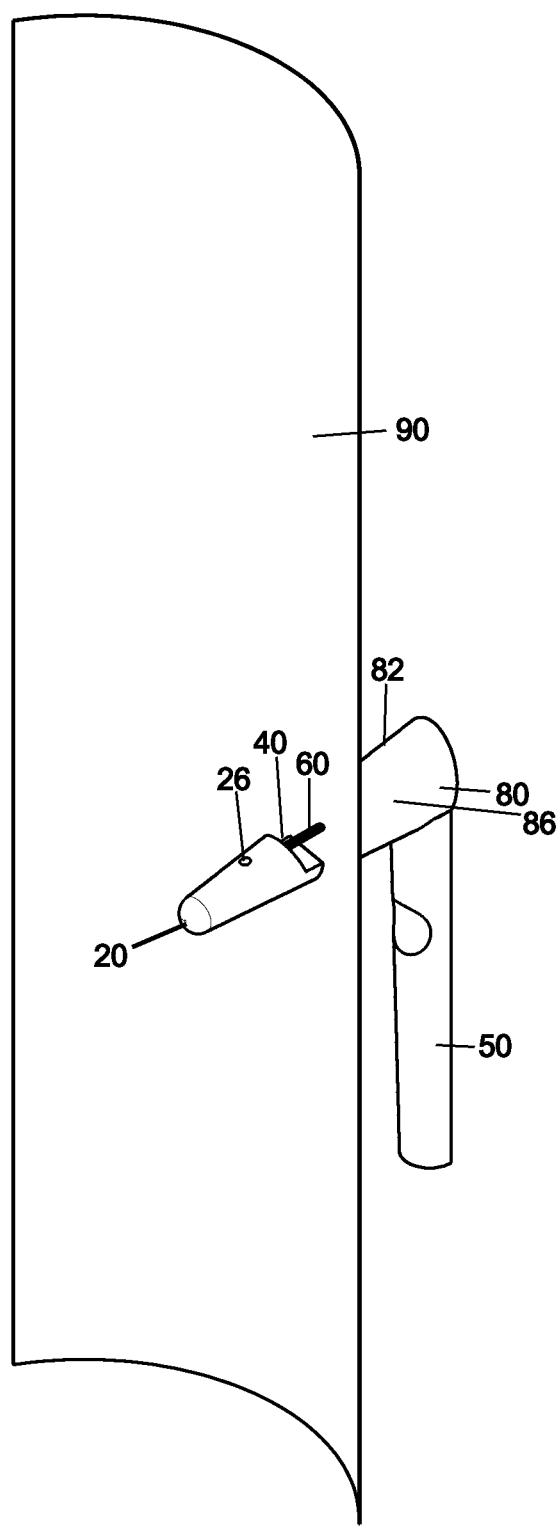
FIG. 13 shows a bottom and front side perspective view of a suturing device with a needle inserted into material, in an embodiment of the disclosed technology.

FIG. 13 shows a bottom and front side perspective view of a suturing device, with a needle inserted into material, in an embodiment of the disclosed technology. The needle 60 is inserted through the needle guide portal shown on the base 10 in FIG. 12. The needle 60 then passes through the needle guide cavity 24, penetrates through the material 90, and extends through the notch 40. The needle 60 then continues passing into the second needle guide portal 25 and into the portion of the needle guide cavity 24 below the notch 40, up to a point between the exit portal 26 and the apex 20 (both the second needle guide portal 25 and the needle guide cavity 24 not being visible in FIG. 13). The needle 60 is visible in the notch 40 beneath the material 90.

The material 90 can include any kind of medium that can be sutured. The suturing device of the disclosed technology can be used with any material 90 where one has access only to one side. Additionally, the suturing device can be used with a material 90 having a pre-existing hole, in order to sew or otherwise close the hole by sewing/attaching the material 90 around the hole. In embodiments, the material 90 can include human tissue (such as human skin or fascia), fabric, synthetics, metals (e.g., screens), and so forth.

Figure 14:
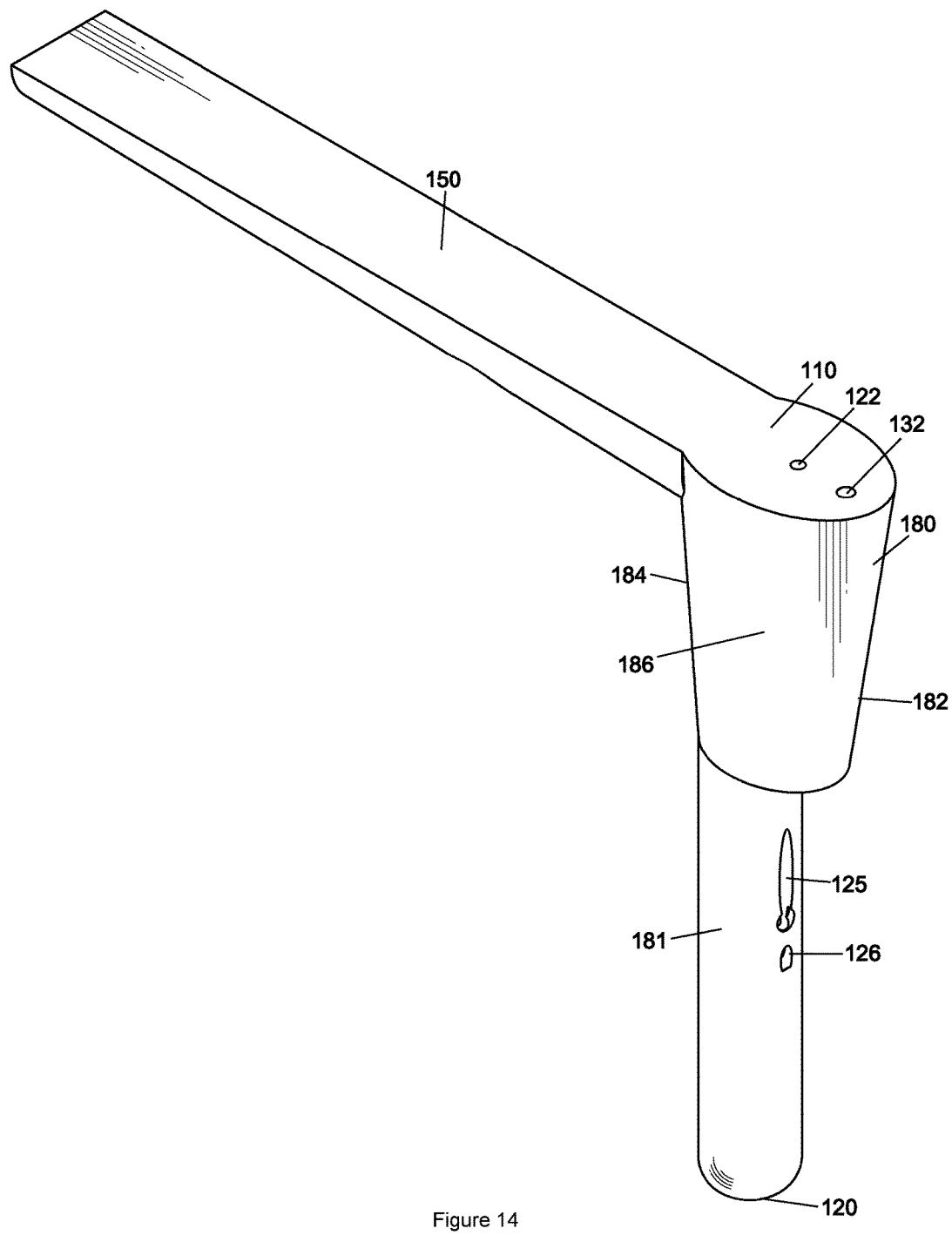
FIG. 14 shows a bottom and front side perspective view of a suturing device, in an embodiment of the disclosed technology.
Figure 15:
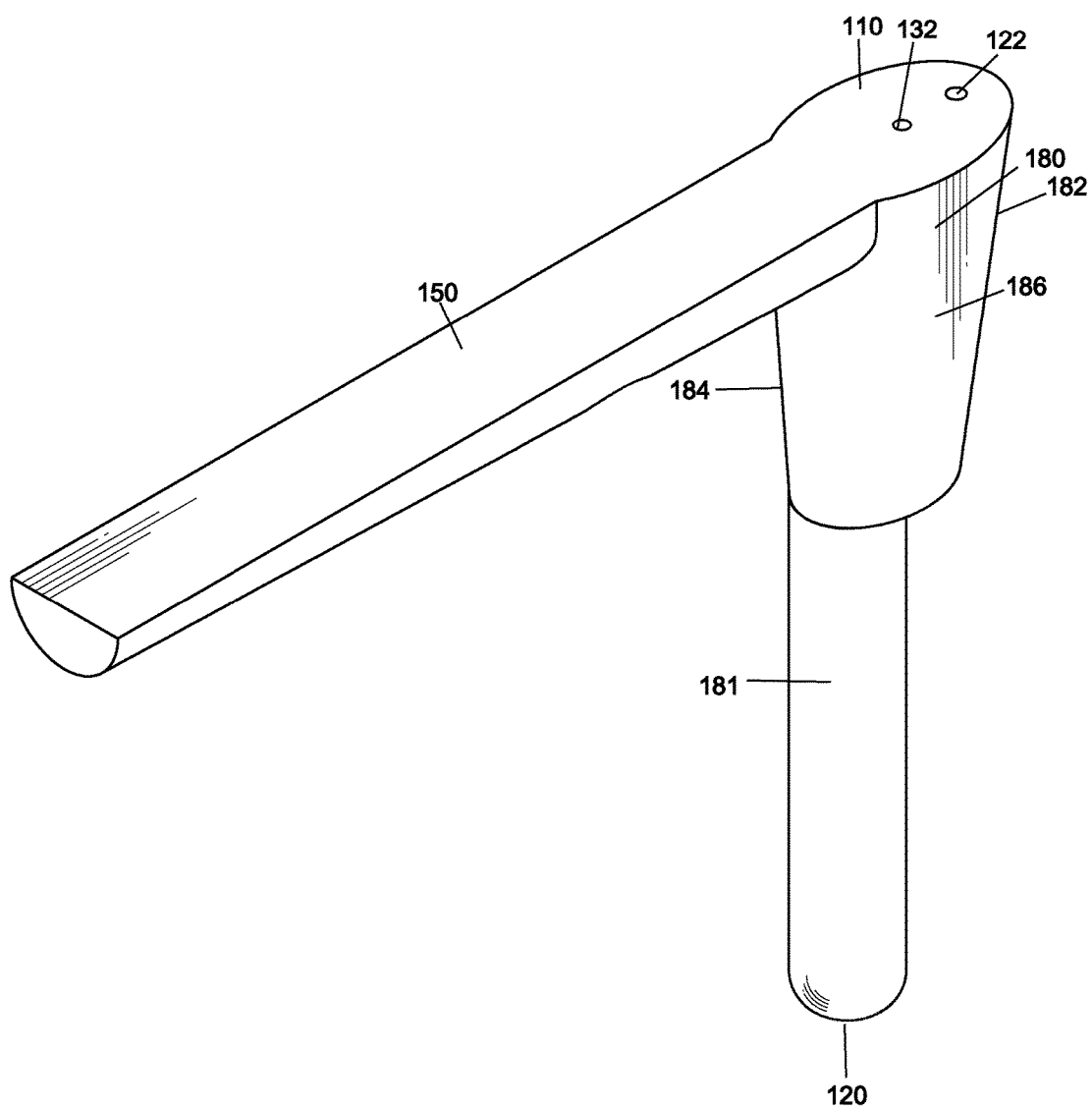
FIG. 15 shows a bottom and back side perspective view of a suturing device, in an embodiment of the disclosed technology.

FIG. 14 shows a bottom and front side perspective view of a suturing device, in an embodiment of the disclosed technology. FIG. 15 shows a bottom and back side perspective view of a suturing device in an embodiment of the disclosed technology. Discussing FIGS. 14 and 15 simultaneously, an alternative embodiment of the suturing device is shown having a uniform bottom portion 181. In this embodiment, an elongated handle 150 joins with a base 110 of a top portion of an elliptical cone 180 of the suturing device of the disclosed technology. The uniform bottom 181 joins with the cone top portion 180 on the back side 184 of the device, opposite the point where the notch 40 is located on the front side 82 of the device, in the embodiments of FIGS. 1-13. The elliptical cone top portion 180 extends between the base 110 and a bottom surface (unnumbered). The bottom portion 181 extends between a point where the bottom portion 181 joins with the top portion 180, and the apex 120.

A needle guide portal 122 is located at the base 110 of the suturing device, and a suture guide portal is located substantially at the base of the suturing device, in embodiments of the disclosed technology. The suture guide portal can be located at the base 110, or closer to the base 110 than the apex 120 of the suturing device. In embodiments, a first exit portal 125 and a second exit portal 126 are located on the front side 182 of the bottom portion 181 of the suturing device. The back side 184 of the elliptical cone portion 180 is adjacent to the elongated handle 150.

Figure 16:
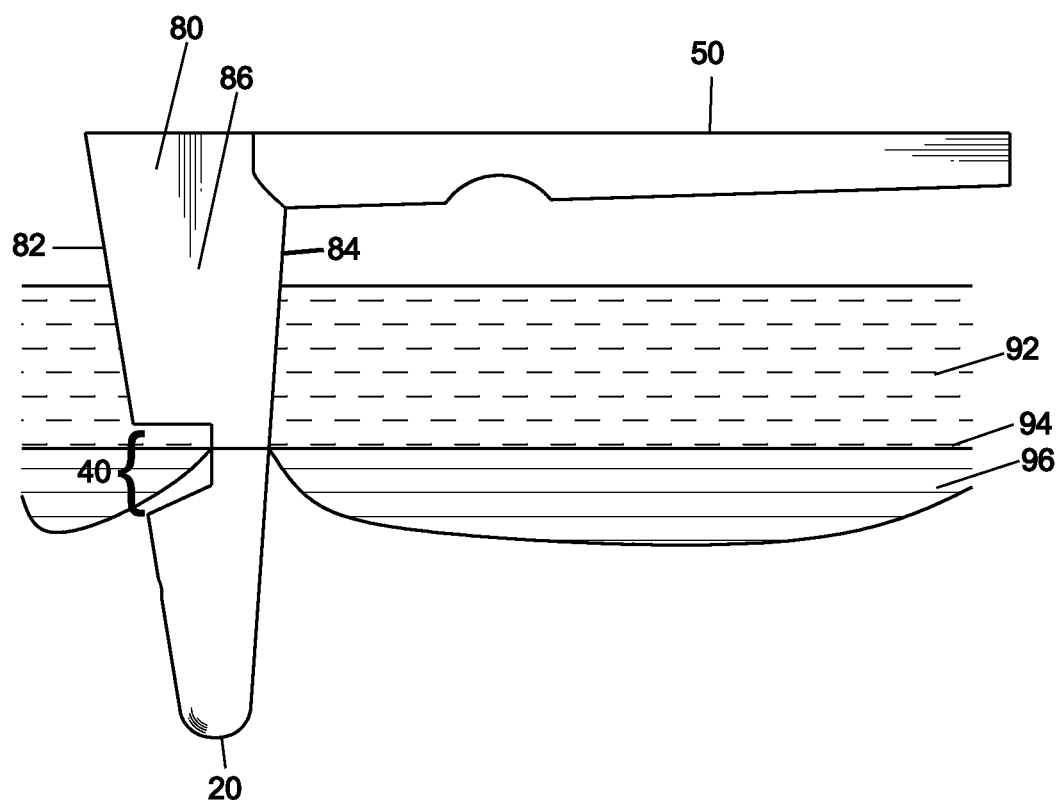
FIG. 16 shows a side elevation view of a suturing device inserted into tissue, in an embodiment of the disclosed technology.

FIG. 16 shows a side elevation view of a suturing device inserted into tissue, in an embodiment of the disclosed technology. In another embodiment of the disclosed technology, the suturing device is inserted into a preexisting hole in material 90 of FIGS. 11-13 that is mammalian or other living tissue in the current embodiment. The apex 20 of the device is inserted through the subcutaneous fat 92, fascia 94, and muscle 96 layers of tissue, so that the layers of tissue are positioned in the notch 40 of the device. The portion of the device extending below the notch 40 to the apex 20 is visible below the subcutaneous fat 92, fascia 94, and muscle 96 layers of tissue. The handle 50 and top portion extending from the base 10 to the notch 40 are visible from above the tissue. In embodiments of the disclosed technology, the suturing device can be used to close a defect in human tissue, specifically a small incision made in a minimally invasive surgical procedure, where there is access only from the outside of the tissue defect.

Figure 17:
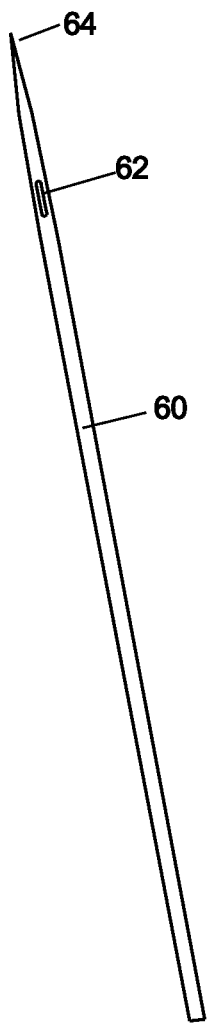
FIG. 17 shows a side view of a needle, in an embodiment of the disclosed technology.
Figure 18:
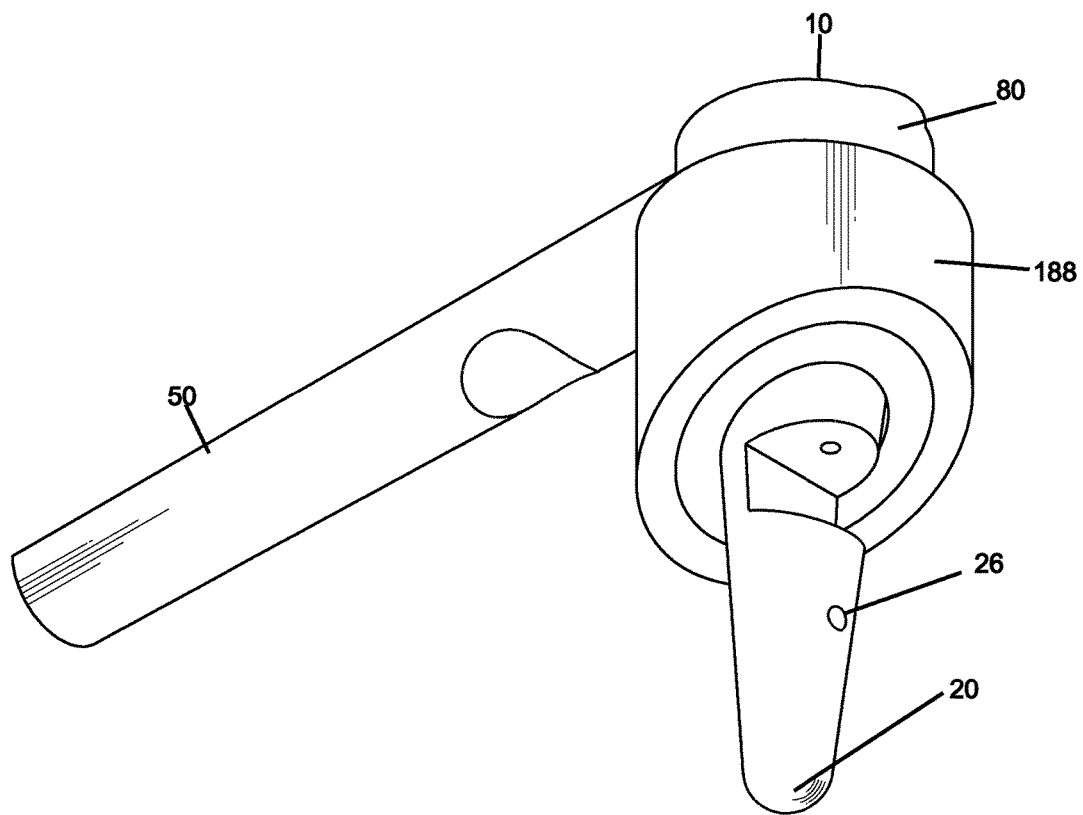
FIG. 18 shows a bottom and front side perspective view of a suturing device wrapped in insulation, in an embodiment of the disclosed technology.

FIG. 17 shows a needle which can be used with the suturing device of FIGS. 1-16 and 18, in an embodiment of the disclosed technology. The needle 60 has a sharp tip 64 and an eye 62. The tip 64 of needle 60 can be inserted into the needle guide portal 22 of FIG. 10 and then passed through the needle guide cavity 24 of FIG. 3. A suture 70 inserted into the suture guide cavity 34 passes through the eye 62 of the inserted needle 60 in FIG. 3, when the eye 62 is aligned with the exit portal 26. The needle 60, in embodiments, can be elliptical (having a flatter and/or more elongated front and back side and narrower left and right sides) matching that of an elliptical portal, such as that of the needle guide portal 22. This ensures that the needle 60 enters the portal in only two orientations, with the eye 62 aligning with the exit portal 26, allowing passage of a suture through the suture portal, eye of the needle, and exit portal.

FIG. 18A shows a bottom and front side perspective view of a suturing device wrapped in insulation, in an embodiment of the disclosed technology. In embodiments of the disclosed technology, at least a portion of the elliptical cone 80 above the notch 40 of the suturing device is wrapped in insulation 188 which can be foam. The insulation 188 encloses the front side 82 of the elliptical cone 80 portion of the device from a point below the base 10, substantially opposite the point where the elongated handle 50 joins with the elliptical cone 80.

The insulation 188 additionally encloses the two sides 86 adjacent to the front side 82 from a point below the base 10, substantially adjacent to where the handle 50 meets the elliptical cone 80, to a point above the notch 40, and above the exit portal 26, in embodiments of the disclosed technology. The back side 84 is enclosed in insulation 188 from a point substantially where the handle 50 meets the elliptical cone 80 below the base 10 of the suturing device, to a point substantially at the apex 20. In embodiments, the elongated handle 50, the base 10, the exit portal 26, the notch 40 and the apex 20 remain visible. FIG. 18B-C shows a cutaway perspective of an embodiment of the disclosed technology as described above.

Figure 19:
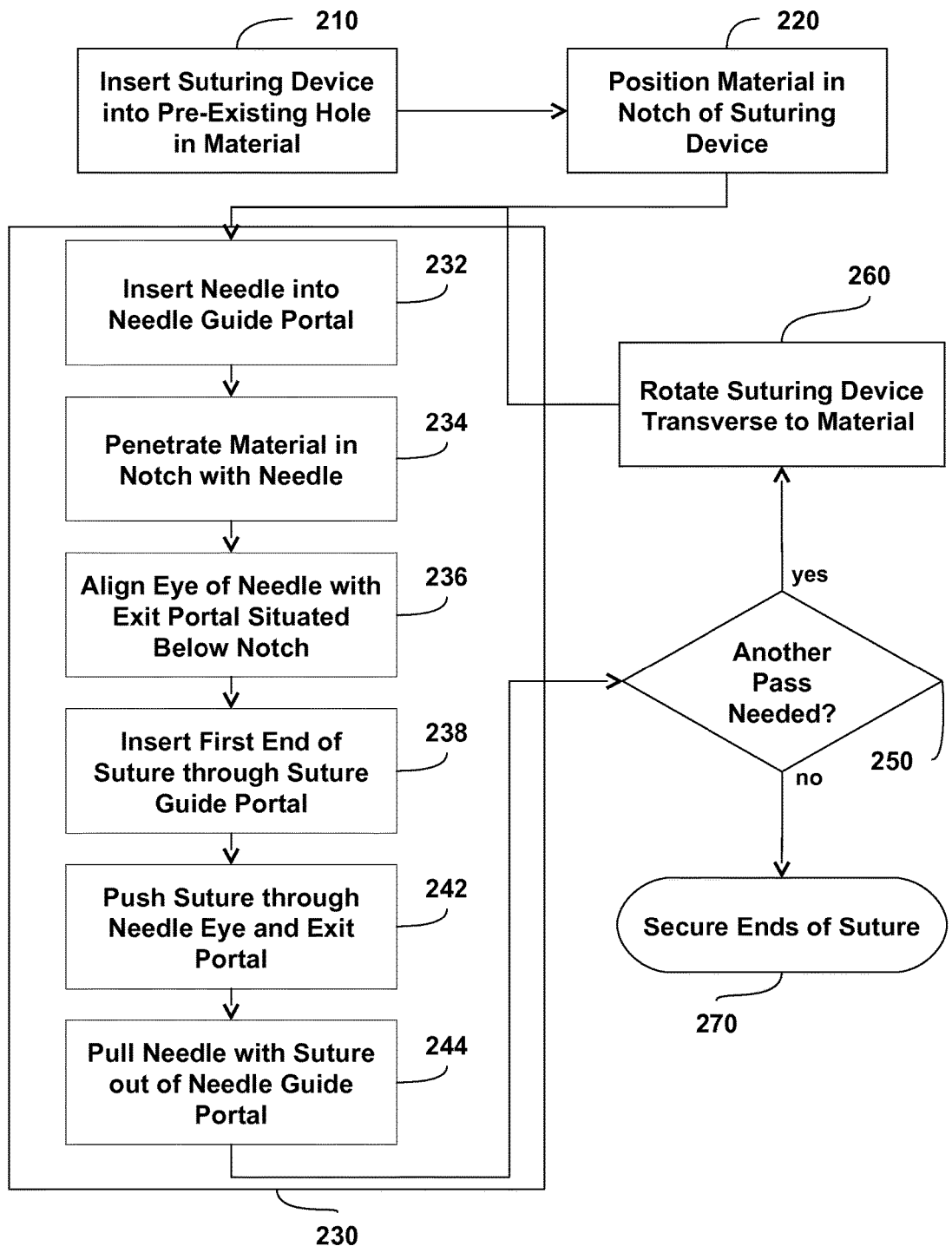
FIG. 19 shows a high level flow chart of a method of suturing a hole with a suturing device, in an embodiment of the disclosed technology.

FIG. 19 shows a high level flow chart of a method of suturing a hole with a suturing device, in an embodiment of the disclosed technology. In a first step 210, the suturing device is inserted into a pre-existing hole in material. The material is then positioned within a notch of the device in step 220. In embodiments without a notch, the material is simply positioned below a needle cavity, so that a needle can be inserted into the material. This is further described in steps 232 and 234, respectively, where a needle is inserted into a needle guide portal and then penetrated into the material. Where a notch (cutout into the body of the suturing device) is present, the material is positioned in the notch and the needle passes through the material, also in the notch.

Then, in step 236, the eye of a needle is aligned with an exit portal of a suture. A suture, or other elongated thread used to sew, is inserted into another portal, such as that located at the top (base) of the suturing device, and extends through a cavity where exiting, at an exit portal, at a location of, or at a height of, an eye of the needle after the needle has passed through the material. This may be accomplished further by way of step 238, inserting the suture into a suture guide portal (step 242), and pushing the suture through the needle eye and an exit portal. Then, in step 244, the needle is pulled out of the suturing device with the suture still passing through the eye of the needle. The needle and suture pass through the material, such that a first half of a stitch is made with the suture extending from the back side of the material (opposite side from a direction of entry of the suturing device). This completes a first pass of the sewing steps of box 230.

After the first pass, another pass will be needed to complete the stitch. As such, in step 250, the decision "yes" is made to another pass being needed. Step 260 is then carried out, and the suturing device is rotated transverse (or orthogonal) to the material. Then, a second end of the suture is inserted and the sewing steps in box 230 are repeated. After completing this second pass, the suture now passes through the material at two spaced-apart locations, with the ends of the suture both extending towards the direction in which the suturing device was inserted (such as outward from the body of a patient being sewn).

More passes can be used, or, alternatively, after decision box 250, step 270 is carried out, and the ends of the suture are secured together, such as by tying. It should further be noted that a portal of the suturing device used for entry of the needle in this method may be elongated, so that a similarly shaped needle can enter only in a direction such that the eye of the needle is perpendicular to the direction of a suture.

Referring again to FIG. 19, the method of use will now be described with reference to the device shown in FIGS. 1-10, as well as such a device shown inserted into material, shown in FIGS. 11-12. In step 210 of embodiments of the method, the suturing device is inserted into a pre-existing hole in a material such as material 90, shown in FIG. 11-13, or tissue, shown in FIG. 16. This may be accomplished by first inserting an apex 20 of the suturing device into a hole. Following the insertion, in step 220, the material 90 is positioned within a notch 40 of the suturing device. The notch, as described above, such as with reference to FIG. 1, is cut into one side of the suturing device between the base 10 and the apex 20 thereof.

In the series of suturing steps 230, the hole is sutured with the device and a needle 60. In the first step of suturing, that is, in step 232, the needle 60 is inserted into a needle guide portal 22 and into the needle guide cavity 24. (The needle may be partially inserted into the needle guide portal before steps 210 and 220). In step 234, after insertion of the needle 60 into the needle guide portal 22, the needle penetrates the material 90 in the notch. This can be seen in FIGS. 11 and 13, FIG. 11 showing the device inserted into the material before the needle, and FIG. 13 showing the needle passing through the material. The needle is inserted into the needle guide portal and can penetrate the material at an angle orthogonal to a plane passing substantially through the hole and the material. In step 236, the needle then passes through the needle guide cavity 24 below the notch, and an eye of the needle 62 is aligned with an exit portal situated between the notch and the apex of the device, such as exit portal 26 shown in FIG. 13.

Still describing the current method, in step 238, a first end of a suture 72 is inserted through a suture guide portal located substantially at the base 20 of the suturing device. The suture then passes through a suture guide cavity, such as suture guide cavity 34, and is pushed through the eye of the needle 52, as well as through the exit portal 26 in step 242, exiting via the exit portal. The angle of the exit of an end 72 (or 74, in a second pass) of the suture 70 can be 90 degrees from the angle of entry of the suture through the suture entry portal 32. In step 244, the needle 60 is then at least partially extracted with the suture from the needle guide portal 22 of the suturing device. In this step, the suture 70, still passing through the eye of the needle, passes back through the material at a point of the needle penetration, pulling the suture there-through.

Following the completion of the series of steps 230, a determination is made as to whether another pass of the needle and suture is needed in step 250. If it is determined that another pass of the needle and suture are needed through the material, in step 260, the suturing device is rotated transverse to the material with respect to the hole, such that another insertion of the needle now can proceed at a second point of penetration of the material. Then, the series of steps 230 are repeated at a second position of the material, and with a second end of the same suture used, or with an additional suture. If it is determined in step 250 that an additional pass in not needed, the suture device may then be extracted from the hole. Once the suture has passed through the second point of penetration, the suture extends both into and out of the material at different points around the hole and can be secured in step 270 of the methods.

Now discussing FIG. 19 in view of FIGS. 11-13 and 16, in embodiments, the pre-existing hole can be a tissue defect, and the material around the hole can constitute bodily tissue. In further embodiments, the method can additionally include a step of removing a trocar from a tissue defect before the step 210 of inserting the suturing device. The step 210 of inserting a suturing device into a pre-existing hole can further include rotating and manipulating the device, while maximizing an amount of tissue positioned in the notch, in embodiments of the disclosed technology. The step 244 of pulling a needle with suture out of needle guide portal can further include completely extracting the needle from the suturing device.

In embodiments, the step 260 of rotating the suturing device can further include rotating the device substantially 180 degrees. Additionally, the suturing device can be elliptical, such that rotating the device substantially 180 degrees causes the tissue defect to stretch, such that first and second points of penetrating are spaced further apart, as compared to carrying out the method with a corresponding circular device, in embodiments of the disclosed technology. The step 270 of securing the ends of the suture can first include a step of extracting the suturing device from the hole. In embodiments, the first suture can be looped through a second suture, such that each end of the first and second sutures can be inserted through the suture guide portal after each step 232 of inserting the needle and each step 234 of penetrating the material.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope.

Combinations of any of the methods, systems, and devices described herein above are also contemplated and within the scope of the invention.

I claim:

1. A suturing kit comprising:
   an elliptical cone with a wider base compared to a narrower apex at opposite ends of said elliptical cone, said base of cone forming a unitary structure with an elongated handle, such that a side of said elliptical cone adjacent to said handle;
   a notch cut into one side of said elliptical cone, extending partially between said base and said apex;
   at least one needle guide cavity, extending in a straight path from a needle guide portal at said base of said cone, through said base of said cone, interrupted by said notch and continuing through said cone, having an exit portal situated between said notch and said apex of said cone, said needle guide cavity terminating before said apex;
   at least one curved suture guide cavity extending between a suture guide portal located substantially at said base of said elliptical cone and opening into said needle guide cavity at a point between said notch and said exit portal; and
   a needle having a length longer than said needle guide cavity and having an eye, said eye aligning with said exit portal when fully inserted in said needle guide portal.

2. The kit of claim 1, wherein said suture guide portal is located at said base of said elliptical cone.

3. The device of claim 1, wherein said needle and at least a part of said needle guide cavity are elliptical.

4. A suturing device kit comprising:
   a suturing device, comprising:
   a base and an apex, said base and said apex being located at opposite ends of said suturing device;
   a notch having a top surface and a bottom surface, and extending into one side of said suturing device, said notch extending partially between said base and said apex;
   at least one needle guide cavity at said base, extending in a straight path through said suturing device, between said base and said notch, and between said notch and said apex;
   an exit portal situated between said bottom surface of said notch and said apex of said suturing device, the exit portal extending into the one side of said suturing device; and
   at least one curved suture guide cavity extending between a suture guide portal located substantially at said base and opening into said needle guide cavity at a point between said notch and said exit portal of said suturing device; and
   a needle having a length that is at least a distance between said base and said exit portal, wherein said needle further comprises an eye, said eye aligning with said exit portal when said needle is inserted in said needle guide cavity.

5. The suturing device of claim 4, wherein said suturing device comprises an elliptical cone formed between said base and said apex of said suturing device.

6. The suturing device of claim 5, wherein said base of said cone forms a unitary structure with a handle.

7. The suturing device of claim 6, wherein said needle guide cavity terminates at a point before said apex.

8. The suturing device of claim 7, wherein said elliptical cone is at least partially wrapped in foam between said notch and said handle.

9. The suturing device kit of claim 4, wherein said needle is longer than said needle guide cavity.

* * * * *